(12) United States Patent
Takayama et al.

(10) Patent No.: US 12,616,957 B2
(45) Date of Patent: *May 5, 2026

(54) BLOCK COPOLYMER, METHOD FOR PRODUCING SAME, AND ABSORBER AND ABSORBENT ARTICLE USING SAME

(71) Applicant: KURARAY CO., LTD., Kurashiki (JP)

(72) Inventors: Takumi Takayama, Kurashiki (JP); Kazuhiko Maekawa, Kurashiki (JP); Kazutoshi Mishima, Kurashiki (JP)

(73) Assignee: KURARAY CO., LTD., Kurashiki (JP)

( * ) Notice: Subject to any disclaimer, the term of this patent is extended or adjusted under 35 U.S.C. 154(b) by 724 days.

This patent is subject to a terminal disclaimer.

(21) Appl. No.: 18/000,970

(22) PCT Filed: Jun. 7, 2021

(86) PCT No.: PCT/JP2021/021513
§ 371 (c)(1),
(2) Date: Dec. 7, 2022

(87) PCT Pub. No.: WO2021/251324
PCT Pub. Date: Dec. 16, 2021

(65) Prior Publication Data
US 2023/0226520 A1 Jul. 20, 2023

(30) Foreign Application Priority Data

Jun. 8, 2020 (JP) ................................. 2020-099593

(51) Int. Cl.
| | |
|---|---|
| *B01J 20/26* | (2006.01) |
| *A23B 2/758* | (2025.01) |
| *A61L 15/24* | (2006.01) |
| *B01J 20/28* | (2006.01) |
| *C08F 297/02* | (2006.01) |
| *A01K 1/015* | (2006.01) |

(52) U.S. Cl.
CPC ............. *B01J 20/264* (2013.01); *A23B 2/758* (2025.01); *A61L 15/24* (2013.01); *B01J 20/28016* (2013.01); *C08F 297/026* (2013.01); *A01K 1/0155* (2013.01); *A01K 1/0157* (2013.01)

(58) Field of Classification Search
CPC .. C08F 216/06; C08F 297/026; C08F 218/08; C08F 220/38; C08F 220/04; C08F 220/64; C08F 222/382; C08F 222/387; C08F 8/12; C08F 220/06; C08F 220/14
See application file for complete search history.

(56) References Cited

U.S. PATENT DOCUMENTS

| | | | |
|---|---|---|---|
| 4,788,242 A | 11/1988 | Takahashi et al. | |
| 4,826,917 A | 5/1989 | Kondo et al. | |
| 12,264,215 B2 * | 4/2025 | Takayama | ............. C08F 297/06 |
| 2022/0267499 A1 * | 8/2022 | Takayama | ............. C08F 4/7095 |

FOREIGN PATENT DOCUMENTS

| | | | |
|---|---|---|---|
| JP | 63-90524 A | 4/1988 | |
| JP | 5-86146 A | 4/1993 | |
| JP | 5-140239 A | 6/1993 | |
| JP | 7-33818 A | 2/1995 | |
| JP | 8-196901 A | 8/1996 | |
| JP | 10-287714 A | 10/1998 | |
| JP | 2004-1461 A | 1/2004 | |
| JP | 2016-155106 A | 9/2016 | |
| WO | WO-2020262517 A1 * | 12/2020 | ............ C08L 53/005 |

OTHER PUBLICATIONS

Extended European Search Report issued Jun. 4, 2024, in corresponding European Patent Application No. 21821781.8, 7 pages.
Kazuhiko Koumura et al: "$Mn_2(CO)_{10}$-induced controlled/living radical copolymerization of vinyl acetate and methyl acylate: Spontaneous formation of block copolymers consisting of gradient and homopolymer segments", Journal of Polymer Science Part A: Polymer Chemistry, vol. 47, No. 5, Mar. 1, 2009, pp. 1343-1353, XP055780925, US, ISSN: 0887-624x, DOI: 10.1002/pola.23243.
International Search Report and English Translation issued Jul. 27, 2021, in PCT/JP2021/021513, filed on Jun. 7, 2021, 6 pages.
Wang et al., "Highly Stretchable Free-Standing Poly(acrylic acid)-block-poly(vinyl alcohol) Films Obtained from Cobalt-Mediated Radical Polymerization, Macromolecules", 2017, vol. 50, pp. 6054-6063.
Debuigne et al., "Synthesis of Novel Well-Defined Poly(vinyl acetate)-b-poly(acrylonitrile) and Derivatized Water-Soluble Poly-(vinyl alcohol)-b-poly(acrylic acid) Block Copolymers by Cobalt-Mediated Radical Polymerization, Macromolecules", 2008, vol. 41, No. 7, pp. 2353-2360.

* cited by examiner

*Primary Examiner* — Mark S Kaucher
(74) *Attorney, Agent, or Firm* — Oblon, McClelland, Maier & Neustadt, L.L.P.

(57) ABSTRACT

A block copolymer (A) including a vinyl alcohol-based polymer block (b) and an ionic polymer block (c) containing a monomer unit with an ionic group forming a salt and a vinyl alcohol-based monomer unit. The ionic group is a carboxylic acid group, a sulfonic acid group, or an ammonium group. The vinyl alcohol-based polymer block (b) has a number-average molecular weight ($Mn_b$) from 15,000 to 220,000. The ionic polymer block (c) has a content of the vinyl alcohol-based monomer unit from 5 to 95 mol % based on the total monomer units. The block copolymer (A) has a number-average molecular weight ($Mn_A$) from 20,000 to 440,000. A ratio ($Mn_b/Mn_A$) of the number-average molecular weight ($Mn_b$) to the number-average molecular weight ($Mn_A$) is from 0.1 to 0.9.

20 Claims, No Drawings

BLOCK COPOLYMER, METHOD FOR PRODUCING SAME, AND ABSORBER AND ABSORBENT ARTICLE USING SAME

CROSS REFERENCE TO RELATED APPLICATIONS

This application is a National Stage entry under 35 U.S.C. § 371 of PCT/JP2021/021513, filed on Jun. 7, 2021, and claims priority to Japanese Patent Application No. 2020-099593, filed on Jun. 8, 2020. The entire contents of both are incorporated herein by reference.

TECHNICAL FIELD

The present invention relates to a block copolymer with excellent absorbency of water, salt water, and the like and to a method for producing the same. The present invention also relates to an absorber and an absorbent article using the block copolymer.

BACKGROUND ART

Conventionally, superabsorbent resins have been widely used for sanitary materials, such as feminine hygiene items and disposable diapers, soil water retention agents, and the like. Known examples of such a superabsorbent resin include polyacrylate crosslinked products, selfcrosslinking polyacrylates, starch-acrylate graft copolymer crosslinked products, hydrolysis products of acrylamide copolymer crosslinked products, neutralized products of crosslinked isobutylene-maleic anhydride copolymers, crosslinked products of carboxyalkyl cellulose salts, and the like.

However, these polymers are crosslinked and insoluble in water and thus are not allowed to be thrown into the sewage, causing a problem of generating a large amount of waste. In addition, these polymers are not sufficiently biodegradable and have a risk of causing soil pollution, marine pollution, and the like, resulting in environmental problems.

Patent Document 1 describes a superabsorbent resin using a crosslinked polymer of an ethylenic unsaturated monomer containing acrylic acid and/or acrylate as a main component. However, such a crosslinked polymer is insoluble in water and insufficiently biodegradable. Patent Document 2 describes an absorber produced by crosslinking a carboxyalkyl cellulose salt or the like with amino acid or the like and further crosslinking the biodegradable water absorbent resin thus obtained with a surface crosslinker. However, the absorber is insoluble in water and sometimes still insufficient in biodegradability.

Meanwhile, polyvinyl alcohols are crystalline water-soluble polymer materials and widely applied to emulsifiers, suspensions, surfactants, fiber treatment agents, various binders, paper processing agents, adhesives, films, and the like using the excellent water solubility and film properties (strength, grease resistance, film formability, oxygen gas barrier properties, etc.).

Non-Patent Documents 1 and 2 describe a block copolymer containing a polyacrylic acid block and a polyvinyl alcohol block and a block copolymer containing a potassium polyacrylate block and a polyvinyl alcohol block. However, some of these block copolymers are insufficient in water absorbency or have difficulty in shape retention after water absorption. In addition, these documents have no description at all of the water absorbency of the block copolymers.

PRIOR ART DOCUMENTS

Patent Documents

Patent Document 1: JP 07-033818 A
Patent Document 2: JP 08-196901 A

Non-Patent Documents

Non-Patent Document 1: Highly Stretchable Free-Standing Poly(acrylic acid)-block-poly(vinyl alcohol) Films Obtained from Cobalt-Mediated Radical Polymerization, Macromolecules, 2017, vol. 50, p 6054-6063

Non-Patent Document 2: Synthesis of Novel Well-Defined Poly(vinyl acetate)-b-poly(acrylonitrile) and Derivatized Water-Soluble Poly(vinyl alcohol)-b-poly(acrylic acid) Block Copolymers by Cobalt-Mediated Radical Polymerization, Macromolecules, 2008, vol. 41, p 2353-2360

SUMMARY OF THE INVENTION

Problems to be Solved by the Invention

The present invention has been made to solve the above problems and it is an object thereof to provide a block copolymer having high absorbency of water, salt water, and the like while also having gel shape retentivity and water solubility.

Means for Solving the Problems

The above problems are solved by providing a block copolymer (A) comprising: a vinyl alcohol-based polymer block (b); and an ionic polymer block (c) containing a monomer unit with an ionic group forming a salt and a vinyl alcohol-based monomer unit, wherein the ionic group is a carboxylic acid group, a sulfonic acid group, or an ammonium group, the polymer block (b) has a number-average molecular weight ($Mn_b$) from 15,000 to 220,000, the ionic polymer block (c) has a content of the vinyl alcohol-based monomer unit from 5 to 95 mol % based on the total monomer units, the block copolymer (A) has a number-average molecular weight ($Mn_A$) from 20,000 to 440,000, and a ratio ($Mn_b/Mn_A$) of the number-average molecular weight ($Mn_b$) to the number-average molecular weight ($Mn_A$) is from 0.1 to 0.9.

In this situation, it is preferable that the ionic group is a carboxylic acid group. It is also preferable that a counterion of the ionic group is an ion of an element in Group 1, 2, 12, 13, or 17 of the periodic table. It is also preferable that the block copolymer (A) has a content ($J_A$) of the monomer unit with an ionic group forming a salt from 2 to 90 mol % based on the total monomer units. It is also preferable that the polymer block (c) has a content ($K_c$) of the monomer unit with an ionic group forming a salt from 5 to 95 mol % based on the total monomer units.

It is also preferable that the block copolymer (A) has a degree of saponification from 80 to 99.99 mol %. It is also preferable that the block copolymer (A) has a molecular weight distribution ($Mw_A/Mn_A$) from 1.05 to 1.95. It is also preferable that the block copolymer (A) is biodegradable.

It is preferable that an amount of deionized water absorbed per 0.1 g of the block copolymer (A) at 20° C. is 20 g or more. It is also preferable that an amount of a 0.9 mass % aqueous sodium chloride solution absorbed per 1 g of the block copolymer (A) at 20° C. is 20 g or more.

It is preferable that, when the block copolymer (A) is dissolved in water at 95° C., a soluble amount is 95 mass % or more and it is more preferable that, when the block copolymer (A) is dissolved in water at 20° C., a soluble amount is 95 mass % or more.

An absorber comprising the block copolymer (A) is a preferred embodiment of the present invention. It is preferable that the absorber is in the form of particles. An absorbent article comprising the absorber is a more preferred embodiment. It is preferable that the absorbent article is used for a sanitary, commodity, construction, civil engineering, industrial, agricultural, medical, or food application.

The above problems are also solved by providing a method for producing the block copolymer (A), the method essentially comprising: a polymerization step of performing polymerization of a vinyl ester monomer and copolymerization of a vinyl ester monomer and an ionic monomer with an ionic group or a derivative thereof by controlled radical polymerization in the presence of a radical polymerization initiator and a control agent to obtain a vinyl ester-based block copolymer having a vinyl ester polymer block (b1) and an ionic polymer block (c1) containing a vinyl ester monomer unit and an ionic monomer unit; and a saponification step of saponifying vinyl ester monomer units in the vinyl ester-based block copolymer obtained in the polymerization step to form vinyl alcohol monomer units, and the method optionally comprising a salt formation step of causing the ionic monomer unit to form a salt.

Effects of the Invention

The block copolymer (A) of the present invention has high absorbency of water, salt water, and the like while also having gel shape retentivity and water solubility. The block copolymer (A) is thus preferably used for absorbers and absorbent articles to water, salt water, and the like. The production method of the present invention allows production of the block copolymer (A).

MODES FOR CARRYING OUT THE INVENTION

The block copolymer (A) of the present invention comprises: a vinyl alcohol-based polymer block (b); and an ionic polymer block (c) containing a monomer unit with an ionic group forming a salt and a vinyl alcohol-based monomer unit, wherein the ionic group is a carboxylic acid group, a sulfonic acid group, or an ammonium group, the polymer block (b) has a number-average molecular weight ($Mn_b$) from 15,000 to 220,000, the ionic polymer block (c) has a content of the vinyl alcohol-based monomer unit from 5 to 95 mol % based on the total monomer units, the block copolymer (A) has a number-average molecular weight ($Mn_A$) from 20,000 to 440,000, and a ratio ($Mn_b/Mn_A$) of the number-average molecular weight ($Mn_b$) to the number-average molecular weight ($Mn_A$) is from 0.1 to 0.9.

The block copolymer (A) of the present invention has high absorbency of water, salt water, and the like while also having gel shape retentivity and water solubility. It is considered that the high absorbency is derived from the ionic polymer block (c) and the gel shape retentivity and the water solubility are derived from the vinyl alcohol-based polymer block (b).

A preferred method for producing the block copolymer (A) of the present invention essentially comprises: a polymerization step of performing polymerization of a vinyl ester monomer and polymerization of a vinyl ester monomer and an ionic monomer with an ionic group or a derivative thereof by controlled radical polymerization in the presence of a radical polymerization initiator and a control agent to obtain a vinyl ester-based block copolymer having a vinyl ester polymer block (b1) and an ionic polymer block (c1) containing a vinyl ester monomer unit and an ionic monomer unit; and a saponification step of saponifying vinyl ester monomer units in the vinyl ester-based block copolymer obtained in the polymerization step to form vinyl alcohol monomer units. The production method is detailed below.

The polymerization step is described at first. In the polymerization step, polymerization of a vinyl ester monomer and polymerization of a vinyl ester monomer and an ionic monomer are performed by controlled radical polymerization in the presence of a radical initiator and a control agent. A vinyl ester is polymerized to synthesize the vinyl ester polymer block (b1), and a vinyl ester monomer and an ionic monomer are polymerized to synthesize the ionic polymer block (c1). In the step of synthesizing the ionic polymer block (c1), an ionic monomer and a vinyl ester monomer are copolymerized to synthesize the ionic polymer block (c1) as a copolymer containing an ionic monomer unit and a vinyl ester monomer unit, causing the block copolymer (A) thus obtained to have improved gel shape retentivity.

Examples of the vinyl ester monomers to be used in the production method of the present invention include vinyl formate, vinyl acetate, vinyl trifluoroacetate, vinyl propionate, vinyl valerate, vinyl butyrate, vinyl isobutyrate, vinyl pivalate, vinyl caprate, vinyl laurate, vinyl stearate, vinyl benzoate, vinyl versatate, and the like. From an economic perspective, vinyl acetate is preferably used.

An ionic monomer to be used in the production method of the present invention is a monomer with an ionic group or a derivative thereof. The ionic group is a carboxylic acid group, a sulfonic acid group, or an ammonium group. They may be used alone or in combination of two or more. The ionic group is preferably a carboxylic acid group. The monomer with such an ionic group may form a salt or may form no salts.

Examples of the monomer with an ionic group or a derivative thereof to be used as the ionic monomer include: monomers with a carboxylic acid group, such as (meth)acrylic acid, maleic acid, itaconic acid, and fumaric acid, and derivatives thereof; monomers with a sulfonic acid group, such as vinylsulfonic acid, allylsulfonic acid, styrenesulfonic acid, 2-(meth)acrylamide-2-methylpropanesulfonic acid, 2-(meth)acryloylethanesulfonic acid, and 2-(meth)acryloylpropanesulfonic acid, and derivatives thereof; and monomers with an ammonium group, such as vinyloxyethyl trimethylammonium chloride, vinyloxybutyl trimethylammonium chloride, N-acrylamide methyl trimethylammonium chloride, 3-(methacrylamide)propyl trimethylammonium chloride, N-acrylamide ethyl trimethylammonium chloride, allyl trimethylammonium chloride, and methallyl trimethylammonium chloride, and derivatives thereof. Among them, monomers with a carboxylic acid group and derivatives thereof are preferred, and monomers with a carboxylic acid group and esters thereof are more preferred.

The monomers with a carboxylic acid group and esters thereof are preferably (meth)acrylic esters. Examples of such a (meth)acrylic ester include methyl (meth)acrylate, ethyl (meth)acrylate, N-propyl (meth)acrylate, i-propyl (meth)acrylate, N-butyl (meth)acrylate, i-butyl (meth)acrylate, t-butyl (meth)acrylate, 2-ethylhexyl (meth)acrylate, dodecyl (meth)acrylate, octadecyl (meth)acrylate, and the like, and methyl (meth)acrylate is more preferred. The (meth)acrylic ester may be a methacrylic ester or an acrylic ester and is more preferably an acrylic ester.

The monomers with a sulfonic acid group are preferably (meth)acrylamide-based monomers, more preferably 2-(meth)acrylamide-2-methylpropanesulfonic acid, and even more preferably 2-acrylamide-2-methylpropanesulfonic acid.

The monomers with an ammonium group are preferably (meth)acrylamide-based monomers and more preferably 3-(methacrylamide)propyl trimethylammonium chloride.

The block copolymer (A) of the present invention may contain, as long as the effects of the present invention are not impaired, a monomer unit derived from an ethylenic unsaturated monomer (e) copolymerizable with the vinyl ester monomers and the ionic monomer. Examples of the ethylenic unsaturated monomer (e) include: olefins, such as ethylene, propylene, 1-butene, and isobutene; acrylamides, such as acrylamide, N-alkyl (carbon number from 1 to 18) acrylamides, and N,N-dimethylacrylamide; methacrylamides, such as methacrylamide, N-alkyl (carbon number from 1 to 18) methacrylamides, and N,N-dimethylmethacrylamide; N-vinylam ides, such as N-vinylpyrrolidone, N-vinylformamide, and N-vinylacetamide; vinyl cyanides, such as acrylonitrile and methacrylonitrile; vinyl ethers, such as alkyl (carbon number from 1 to 18) vinyl ethers, hydroxyalkyl vinyl ethers, and alkoxyalkyl vinyl ethers; vinyl halides, such as vinyl chloride, vinylidene chloride, vinyl fluoride, vinylidene fluoride, and vinyl bromide; vinyl silanes, such as trimethoxyvinyl silane; allyl compounds, such as allyl acetate, allyl chloride, allyl alcohol, and dimethylallyl alcohol; and the like. When being used, the ethylenic unsaturated monomer (e) may be copolymerized during the polymerization to form the vinyl ester polymer block (b1), may be copolymerized during the polymerization to form the ionic polymer block (c1), or may be polymerized separately from the polymerization to form the vinyl ester polymer block (b1) and the ionic polymer block (c1).

The vinyl alcohol-based polymer block (b) and the ionic polymer block (c), both constituting the block copolymer (A), have a content of the ethylenic unsaturated monomer (e) of preferably 10 mol % or less based on the total monomer units in the respective blocks, more preferably 3 mol % or less, even more preferably 1 mol % or less, and particularly preferably substantially do not contain the ethylenic unsaturated monomer (e). The block copolymer (A) has a content of the ethylenic unsaturated monomer (e) of preferably 10 mol % or less based on the total monomer units, more preferably 3 mol % or less, even more preferably 1 mol % or less, and particularly preferably substantially do not contain the ethylenic unsaturated monomer (e).

The controlled radical polymerization employed in the production method of the present invention is polymerization reaction where reaction proceeds in an equilibrium state between a propagating radical end (active species) and a covalent species (dormant species) formed by the propagating radical end bonded with a control agent. Examples of the control agent to be used in the production method of the present invention include organic cobalt complexes, organic iodine compounds, thiocarbonyl compounds, organic tellurium compounds, organic compounds with a redox center, organic compounds with a stable radical, and the like. Among them, organic cobalt complexes are preferred.

Examples of such an organic cobalt complex include those containing a divalent cobalt atom and an organic ligand. Examples of preferred organic cobalt complexes include cobalt(II) acetylacetonate [Co(acac)$_2$], cobalt(II)

porphyrin complexes, and the like. Among them, cobalt(II) acetylacetonate is preferred from the perspective of production costs.

Examples of the polymerization method include known methods, such as bulk polymerization, solution polymerization, suspension polymerization, and emulsion polymerization. Among all, bulk polymerization in which polymerization is conducted in a nonsolvent system or solution polymerization in which polymerization is conducted in various organic solvents is usually employed. In order to obtain a polymer having a narrow molecular weight distribution, a bulk polymerization method is preferred, which does not use a solvent or a dispersion medium having a possibility of causing side reactions, such as chain transfer.

Meanwhile, solution polymerization is sometimes preferred from the perspective of viscosity control of the reaction liquid, control of the polymerization rate, and the like. Examples of the organic solvent used as the solvent in solution polymerization include: esters, such as methyl acetate and ethyl acetate; aromatic hydrocarbons, such as benzene and toluene; lower alcohols, such as methanol and ethanol; and the like. Among them, esters and aromatic hydrocarbons are preferably used to prevent chain transfer. In the case of using such a solvent, the amount of the solvent to be used may be determined considering the viscosity of the reaction solution in accordance with the number-average molecular weight of the target block copolymer (A). For example, the amount may be selected from a range of mass ratio (solvent/monomer) from 0.01 to 10. The mass ratio (solvent/monomer) is preferably 0.1 or more and preferably 5 or less.

As the radical initiator to be used in the polymerization step, conventionally known azo initiators, peroxide initiators, redox initiators, and the like are appropriately selected. Examples of the azo initiators include 2,2'-azobisisobutyronitrile, 2,2'-azobis(2,4-dimethylvaleronitrile), 2,2'-azobis(4-methoxy-2,4-dimethylvaleronitrile), and the like. Examples of the peroxide initiators include: percarbonate compounds, such as diisopropyl peroxydicarbonate, di-2-ethylhexyl peroxydicarbonate, and diethoxyethyl peroxydicarbonate; perester compounds, such as t-butyl peroxyneodecanoate, α-cumyl peroxyneodecanoate, and t-butyl peroxyneodecanoate; acetylcyclohexylsulfonyl peroxide; diisobutyryl peroxide; 2,4,4-trimethylpentyl-2-peroxyphenoxyacetate; and the like. Moreover, the above initiator may be combined with potassium persulfate, ammonium persulfate, hydrogen peroxide, or the like to be used as an initiator. Examples of the redox initiators include combinations of the above peroxides with reducing agents, such as sodium hydrogen sulfite, sodium hydrogen carbonate, tartaric acid, L-ascorbic acid, and Rongalite. The amount of the initiator to be used varies depending on the polymerization catalyst and is not unconditionally determined, and is arbitrarily selected in accordance with the polymerization rate.

In the controlled radical polymerization used in the present invention, firstly, the radical initiator is decomposed to generate radicals and the radicals are bonded with a small number of monomers to yield a short-chain polymer having a radical at the propagating end, and the radical is covalently bonded with the control agent to yield a dormant species. In a certain period after the start of the reaction, such a short-chain polymer is yielded only to be converted to a dormant species and thus the degree of polymerization substantially does not increase. This period is referred to as an induction period. After consumption of the control agent, a growth period begins in which the degree of polymerization increases and most molecular chains in the reaction system have a molecular weight similarly increasing in proportion to polymerization time. This allows production of a vinyl ester-based block copolymer having a narrow molecular weight distribution. The time taken for the polymerization step of monomers in total of the induction period and the growth period is usually from 3 to 50 hours.

As described above, in the controlled radical polymerization of the present invention, one polymer chain is theoretically yielded from one molecule of the control agent to be added. Accordingly, the amount of the control agent to be added to the reaction liquid is determined in consideration of a desired number-average molecular weight and a desired rate of polymerization. Usually, it is preferable to use 0.001 to 1 mol of the control agent based on 100 mol of the monomer.

The number of moles of the generated radicals not more than the number of moles of the control agent causes the polymerization reaction to proceed only by a mechanism in which the control agent is thermally dissociated from the dormant species, resulting in an extremely low polymerization rate depending on the reaction temperature. Therefore, considering that the radical initiator generates two radicals, the number of moles of the radical initiator to be used has to be more than $\frac{1}{2}$ times the number of moles of the control agent. Since the amount of active radicals supplied from the initiator generally depends on the initiator efficiency, some of the initiator is actually deactivated without being used for the formation of the dormant. Therefore, the number of moles of the radical initiator to be used is preferably 1 time or more and more preferably 1.5 times or more the number of moles of the control agent. Meanwhile, the number of moles of the generated radicals excessively more than the number of moles of the control agent causes an increase in the ratio of uncontrolled radical polymerization and thus the molecular weight distribution broadens. The number of moles of the radical initiator to be used is preferably 10 times or less and more preferably 6 times or less the number of moles of the control agent.

The method for mixing the radical initiator, the control agent, and the monomer is not particularly limited as long as the method is capable of generating the dormant species and controlling the increase in the degree of polymerization of the polymer. Examples of the method include: a method comprising mixing the radical initiator and the control agent, followed by mixing the mixture thus obtained with the monomer; a method comprising mixing the radical initiator, the control agent, and the monomer at one time; a method comprising mixing the control agent and the monomer, followed by mixing the mixture thus obtained with the radical initiator; and the like. The radical initiator, the control agent, and the monomer may be mixed dividedly. Examples of such a method include a method in which the radical initiator, the control agent, and a part of the monomer are mixed to generate a dormant species in which the control agent is covalently bonded with a short-chain polymer end, and then the dormant species and the rest of the monomer are mixed to increase the degree of polymerization. The dormant species may be isolated as a macroinitiator, and then mixed with the rest of the monomer to increase the degree of polymerization.

In the polymerization step, either the synthesis of the vinyl ester polymer block (b1) or the synthesis of the ionic polymer block (c1) may be performed first. When the synthesis of the vinyl ester polymer block (b1) is performed first, the polymerization of the vinyl ester monomer is started by mixing the vinyl ester monomer, the ethylenic unsaturated monomer (e) if necessary, the radical initiator, and the control agent by the above-described method. It is preferable not to use an ionic monomer in the synthesis of the vinyl ester polymer block (b1).

After the number-average degree of polymerization of the vinyl ester polymer block (b1) reaches a target value, the vinyl ester monomer and the ionic monomer are polymerized to perform synthesis of the ionic polymer block (c1). In this situation, the ionic monomer may be added to the reaction liquid after removing the remaining vinyl ester monomer to start the polymerization of the ionic monomer, whereas the ionic monomer is preferably added to the reaction liquid without removing the vinyl ester monomer to start the copolymerization of the remaining vinyl ester monomer and the ionic monomer from the perspective of further improving the gel shape retentivity. The method for adding the ionic monomer is not particularly limited, and examples of the method include a method comprising adding all at once, a method comprising feeding with time, and the like. From the perspective of further improving the gel shape retentivity due to the uniform introduction of the ionic monomer unit, the latter is preferred. If necessary, an additional vinyl ester monomer and ethylenic unsaturated monomer (e) may be added together with the ionic monomer. The number-average degree of polymerization of the polymer can be checked by GPC (gel permeation chromatography), and specifically, a method described in Examples described later is adopted.

When the synthesis of the vinyl ester polymer block (b1) is performed first, in the case of obtaining a binary vinyl ester-based block copolymer having one vinyl ester polymer block (b1) and one copolymer block (c1) containing a vinyl ester monomer unit and an ionic monomer unit, the reaction is preferably terminated before the ionic monomer disappears. Meanwhile, in the case of obtaining a ternary or more multicomponent vinyl ester-based block copolymer, the polymerization is preferably continued even after the ionic monomer disappears to synthesize a vinyl ester polymer block (b1). By this method, a ternary vinyl ester-based block copolymer of block (b1)-block (c1)-block (b1) can be obtained. In the present invention, a part obtained by polymerizing the vinyl ester in a state in which the molar ratio of the ionic monomer unit to the vinyl ester in the reaction liquid (ionic monomer/vinyl ester) is 0.00001 or less is defined as a vinyl ester polymer block (b1). The time point at which the molar ratio (ionic monomer/vinyl ester) reaches 0.00001 is determined by the method described in the Examples. When the number-average degree of polymerization of the vinyl ester-based block copolymer reaches a target value, the reaction may be terminated. In the case of obtaining a quaternary or more multicomponent vinyl ester-based block copolymer, an ionic monomer may be added again to the reaction liquid of the ternary vinyl ester-based block copolymer to continue the polymerization.

When the synthesis of the ionic polymer block (c1) is performed first in the polymerization step, the polymerization is started by mixing the ionic monomer, the radical initiator, and the organic cobalt complex by the method described above. In this situation, from the perspective of further improving the gel shape retentivity, it is preferable to further add a vinyl ester monomer. If necessary, an ethylenic unsaturated monomer (e) may be further added. The polymer block (c1) containing a vinyl ester monomer unit and an ionic monomer unit is thus synthesized, and then the respective blocks are sequentially formed.

The vinyl ester polymer block (b1) and the ionic polymer block (c1) are preferably synthesized at a polymerization temperature, for example, from 0° C. to 80° C. A polymerization temperature of less than 0° C. causes an insufficient polymerization rate and thus productivity is prone to be reduced. In this regard, the polymerization temperature is more preferably 10° C. or more and even more preferably 20° C. or more. Meanwhile, a polymerization temperature of more than 80° C. is prone to cause broadening of the molecular weight distribution of the resulting block copolymer (A). In this regard, the polymerization temperature is more preferably 65° C. or less and even more preferably 50° C. or less.

When the number-average degree of polymerization or the rate of polymerization of the vinyl ester-based block copolymer reaches a target value in the polymerization step, it is preferable to perform a terminating step of terminating the polymerization reaction by adding a polymerization terminator. Examples of the polymerization terminator include: 1,1-diphenylethylene; styrene compounds, such as styrene, α-methylstyrene, and 4-tert-butylstyrene; aromatic hydroxy compounds, such as p-methoxyphenol, hydroquinone, cresol, t-butylcatechol, and p-nitrosophenol; quinone compounds, such as benzoquinone and naphthoquinone; conjugated carboxylic acids, such as muconic acid and sorbic acid; thioethers, such as phenothiazine, distearyl thiodipropionate, and dilauryl thiodipropionate; aromatic amines, such as p-phenylenediamine and N-nitrosodiphenylamine; nitroxides, such as 2,2,6,6-tetramethylpiperidine 1-oxyl and 4-hydroxy-2,2,6,6-tetramethylpiperidine 1-oxyl; transition metal salts, such as copper acetate, copper dithiocarbamate, and manganese acetate; and the like. Among them, 1,1-diphenylethylene, sorbic acid, and benzoquinone are preferred and 1,1-diphenylethylene is more preferred.

The number of moles of the polymerization terminator to be added is preferably from 1 to 100 mol per mole of the control agent added. An excessively small number of moles of the polymerization terminator causes a risk of not sufficiently trapping radicals at polymer ends to deteriorate color tone of the block copolymer (A) to be obtained. Meanwhile, an excessively large number of moles of the polymerization terminator causes a risk of increasing production costs.

The temperature of the reaction liquid in the terminating step may be any temperature at which the polymerization terminator is capable of reacting with a radical at the end of the vinyl ester-based block copolymer, and is preferably from 0° C. to 80° C. The time taken for the terminating step is usually from 10 minutes to 5 hours.

When a cobalt complex is used as the control agent, it is preferable to perform, before the saponification step, an extraction step of bringing the vinyl ester-based block copolymer solution thus obtained into contact with an aqueous solution containing a water-soluble ligand to extract and remove the cobalt complex from the vinyl ester-based block copolymer solution. As just described, the saponification step performed after removal in advance of the cobalt complex contained in the vinyl ester-based block copolymer solution allows production of a block copolymer (A) with good hue. Specifically, such a copolymer may be obtained by performing an operation that comprises vigorously stirring the aqueous solution and the vinyl ester-based block copolymer solution, which are mutually insoluble, to cause their interface have an increased area, leaving them at rest to separate into an oil layer and an aqueous layer, and then removing the aqueous layer. This operation may be repeated a plurality of times.

The water-soluble ligand to be used in the extraction step is preferably an acid having a pKa from 0 to 12 at 25° C. In the case of using a strong acid having a pKa of less than 0, it is difficult to efficiently extract the cobalt complex, and the pKa is preferably 2 or more. Also, in the case of using a weak acid having a pKa of more than 12, it is difficult to efficiently extract the cobalt complex, and the pKa is preferably 7 or less. When the acid is a polyvalent acid, the first dissociation constant (pKa1) has to be in the above range. The acid having a pKa from 0 to 12 as the water-soluble ligand is preferably a carboxylic acid or a phosphoric acid (pKa1 of 2.1) and more preferably a carboxylic acid. Among them, acetic acid (pKa of 4.76) is particularly preferred.

The aqueous solution containing the water-soluble ligand preferably has a pH from 0 to 5. The pH is more preferably 1 or more and even more preferably 1.5 or more. The pH is more preferably 4 or less and even more preferably 3 or less.

In the saponification step, the vinyl ester monomer units contained in the vinyl ester polymer block (b1) and the ionic polymer block (c1) in the vinyl ester-based block copolymer obtained in the polymerization step are saponified to form vinyl alcohol monomer units. The saponification step causes the vinyl ester polymer block (b1) to be converted to the vinyl alcohol-based polymer block (b).

In the saponification step, the vinyl ester-based block copolymer produced by the method described earlier is saponified in a state of being dissolved in an alcohol, and thus the vinyl ester monomer unit in the vinyl ester-based block copolymer is converted to a vinyl alcohol monomer unit. When the vinyl ester-based block copolymer obtained using an acrylic ester as the ionic monomer is saponified, an acrylic ester monomer unit in the copolymer may be converted to an acrylic acid monomer unit and the acrylic acid monomer unit thus converted may form a salt. Moreover, the acrylic acid ester monomer unit or the acrylic acid monomer unit may form a lactone ring with an adjacent vinyl alcohol monomer unit.

Examples of the alcohol to be used in the saponification reaction include lower alcohols, such as methanol and ethanol, and methanol is particularly preferably used. The alcohol may be hydrous alcohol or dehydrated alcohol. The alcohol to be used in the saponification reaction may contain a solvent, such as acetone, an ester, such as methyl acetate or ethyl acetate, or toluene. Examples of the catalyst to be used in the saponification reaction include hydroxides of alkali metals, such as potassium hydroxide and sodium hydroxide; alkaline catalysts, such as sodium methylate; and acid catalysts, such as mineral acids. An appropriate range of the temperature of the saponification reaction is, for example, from 20° C. to 70° C. When a gelatinous product is precipitated with progress of the saponification reaction, the product is ground at that timing and washed, followed by being dried.

The production method of the present invention optionally comprises a salt formation step of causing the ionic monomer unit in the block copolymer after the saponification step to form a salt. The method for causing the ionic monomer unit to form a salt is not particularly limited, and a known method may be appropriately employed in accordance with the type of ionic monomer unit. The saponification step and the salt formation step cause the ionic polymer block (c1) to be converted to the ionic polymer block (c) containing the monomer unit with an ionic group forming a salt and the vinyl alcohol-based monomer unit. It should be noted that, when the ionic polymer block (c1) after the saponification step contains the monomer unit with the ionic group forming a salt, the block (c1) is equivalent to the block (c) and thus it is possible to obtain the block copolymer (A) of the present invention without the salt formation step.

When an acrylic ester is used as the ionic monomer, the block copolymer after the saponification step is preferably subjected to the salt formation step. This causes the acrylic ester unit, the acrylic acid unit, and the lactone ring to be converted to acrylic acid monomer units forming a salt. Examples of a specific method include a method comprising mixing the block copolymer after the saponification step with an aqueous solution of a metal hydroxide and an alcohol, and the like. Examples of the metal hydroxide include sodium hydroxide, potassium hydroxide, calcium hydroxide, and the like. Examples of the alcohol include methanol, ethanol, and the like. The salt formation step is appropriately performed in a range, for example, from 20° C. to 100° C.

The monomer unit with an ionic group in the ionic polymer block (c) is formed by the ionic monomer described above. The ionic group is a carboxylic acid group, a sulfonic acid group, or an ammonium group, and among them, a carboxylic acid group is preferred. The monomer unit with an ionic group is as described above, and among all, a monomer unit with a carboxylic acid group is preferred and an acrylic acid monomer unit is more preferred.

The monomer unit with an ionic group in the ionic polymer block (c) forms a salt. A counterion of the monomer unit is not particularly limited and is preferably an ion of an element in Group 1, 2, 12, 13, or 17 of the periodic table. Among them, the counterion is preferably: a cation, such as a sodium ion, a potassium ion, a magnesium ion, a calcium ion, a zinc ion, and an aluminum ion; or an anion, such as a chloride ion. The cation is more preferably a sodium ion and a calcium ion and even more preferably a sodium ion.

The block copolymer (A) of the present invention thus obtained comprises: the vinyl alcohol-based polymer block (b); and the ionic polymer block (c) containing the monomer unit with the ionic group forming a salt and the vinyl alcohol-based monomer unit. The block copolymer (A) may be a binary block copolymer composed of one block (b) and one block (c), or may be a ternary block copolymer composed of one block (b) and two blocks (c) or composed of two blocks (b) and one block (c), or may be a multi-block copolymer composed of totally four or more blocks (b) and block (c). Among them, the block copolymer (A) is preferably a binary block copolymer or a ternary block copolymer. The bonding form of the block (b) with the block (c) is preferably linear. The block copolymer (A) may contain a block other than the block (b) and the block (c), preferably with a content of 10 mol % or less and more preferably 1 mol % or less.

The block copolymer (A) of the present invention preferably has a degree of saponification from 80 to 99.99 mol %. In the present invention, the saponification degree refers to the ratio (mol %) of the number of moles of the vinyl alcohol monomer units to the total number of moles of the vinyl ester monomer units and the vinyl alcohol monomer units in the block copolymer (A). A saponification degree of less than 80 mol % causes the block copolymer to have too low crystallinity and thus a decrease in the gel shape retentivity, resulting in a risk of not providing desired absorption performance. The degree of saponification is preferably 85 mol % or more, more preferably 90 mol % or more, and even more preferably 95 mol % or more. Meanwhile, a degree of saponification of more than 99.99 mol % tends to cause difficulty in the production of the block copolymer (A). Preferably, the saponification degree is 99.95 mol % or less. The degree of saponification can be determined by $^1$H-NMR measurement of the vinyl alcohol-based block copolymer (A), and specifically, the method described in Examples is employed.

The block copolymer (A) of the present invention preferably has a content ($Z_A$) of a unit derived from the ionic monomer with an ionic group or a derivative thereof from 2 to 90 mol % based on the total monomer units. When an acrylic ester is used as the ionic monomer, the unit derived from the ionic monomer includes an acrylic acid monomer unit forming a salt, an acrylic acid monomer unit not forming a salt, an acrylic acid ester monomer unit, and a lactone ring, and the content ($Z_A$) is a total amount of these units.

The content ($Z_A$) of 2 mol % or more causes a further increase in the absorbency of the block copolymer (A). The content ($Z_A$) is more preferably 3 mol % or more, even more preferably 4 mol % or more, and particularly preferably 5 mol % or more. Meanwhile, the content ($Z_A$) of 90 mol % or less allows further improvement of the gel shape retentivity of the block copolymer (A). The content ($Z_A$) is more preferably 60 mol % or less, more preferably 40 mol % or less, and particularly preferably 20 mol % or less.

The block copolymer (A) of the present invention preferably has a content ($J_A$) of the monomer unit with an ionic group forming a salt from 2 to 90 mol % based on the total monomer units. The content ($J_A$) of 2 mol % or more causes a further increase in the absorbency of the block copolymer (A). The content ($J_A$) is more preferably 3 mol % or more, even more preferably 4 mol % or more, and particularly preferably 5 mol % or more. Meanwhile, the content ($J_A$) of 90 mol % or less allows further improvement of the gel shape retentivity of the block copolymer (A). The content ($J_A$) is more preferably 60 mol % or less, more preferably 40 mol % or less, and particularly preferably 20 mol % or less.

The vinyl alcohol-based polymer block (b) preferably has a content of the vinyl alcohol-based monomer unit of 80 mol % or more based on the total monomer units, more preferably 90 mol % or more, even more preferably 95 mol % or more, and particularly preferably 99 mol % or more. In the present invention, the vinyl alcohol-based monomer unit means a vinyl ester monomer unit and a vinyl alcohol monomer unit, and the content of the vinyl alcohol-based monomer unit means the total content of the vinyl ester monomer unit and the vinyl alcohol monomer unit.

The vinyl alcohol-based polymer block (b) preferably has a content of the vinyl alcohol monomer unit of 80 mol % or more based on the total monomer units, more preferably 90 mol % or more, even more preferably 95 mol % or more, and particularly preferably 99 mol % or more.

The vinyl alcohol-based polymer block (b) usually has a content of the unit derived from the ionic monomer of less than 0.1 mol % based on the total monomer units.

The ionic polymer block (c) preferably has a content ($R_c$) of the unit derived from the ionic monomer from 5 to 95 mol % based on the total monomer units. The content ($R_c$) of 5 mol % or more causes a further increase in the absorbency of the block copolymer (A). The content ($R_c$) is more preferably 6 mol % or more, even more preferably 8 mol % or more, and particularly preferably 10 mol % or more. Meanwhile, from the perspective of further improving the gel shape retentivity of the block copolymer (A), the content ($R_c$) is more preferably 80 mol % or less, even more preferably 40 mol % or less, and particularly preferably 25 mol % or less.

The ionic polymer block (c) preferably has a content ($K_c$) of the monomer unit with the ionic group forming a salt from 5 to 95 mol % based on the total monomer units. The content ($K_c$) of 5 mol % or more causes a further increase in the absorbency of the block copolymer (A). The content ($K_c$) is more preferably 6 mol % or more, even more preferably 8 mol % or more, and particularly preferably 10 mol % or more. Meanwhile, from the perspective of further improving the gel shape retentivity of the block copolymer (A), the content ($K_c$) is more preferably 80 mol % or less, even more preferably 40 mol % or less, and particularly preferably 25 mol % or less.

The ionic polymer block (c) contains the vinyl alcohol-based monomer unit. This causes the block copolymer (A) to have improved gel shape retentivity and absorbency. The ionic polymer block (c) has a content of the vinyl alcohol-based monomer unit (total content of the vinyl alcohol unit and the vinyl ester unit) from 5 to 95 mol % based on the total monomer units. If the content is less than 5 mol %, the block copolymer (A) is not allowed to have the effects of improving the gel shape retentivity and the absorbency. The content is preferably 20 mol % or more, more preferably 60 mol % or more, and even more preferably 75 mol % or more. Meanwhile, if the content of the vinyl alcohol-based monomer unit is more than 95 mol %, the block copolymer (A) has reduced absorbency. The content is preferably 94 mol % or less, more preferably 92 mol % or less, and even more preferably 90 mol % or less.

The block copolymer (A) of the present invention has a number-average molecular weight ($Mn_A$) from 20,000 to 440,000. Use of controlled polymerization allows production of the block copolymer (A) having a narrow molecular weight distribution and a high number-average molecular weight ($Mn_A$). The $Mn_A$ of 20,000 or more causes the block copolymer (A) to have improved absorbency. The $Mn_A$ is preferably 30,000 or more, more preferably 40,000 or more, even more preferably 50,000 or more, and particularly preferably 60,000 or more. Meanwhile, the $Mn_A$ of 440,000 or less allows improvement of the gel shape retentivity. The $Mn_A$ is preferably 300,000 or less, more preferably 250,000 or less, and even more preferably 200,000 or less. The number-average molecular weight ($Mn_A$) and the molecular weight distribution ($Mw_A/Mn_A$) are values determined by measuring the block copolymer (A) with a tetrahydrofuran (THF)-based column using polymethyl methacrylate as a reference material by GPC. The measurement method is described in Examples.

The vinyl alcohol-based polymer block (b) has a number-average molecular weight ($Mn_b$) from 15,000 to 220,000. When the block copolymer (A) contains a plurality of the vinyl alcohol-based polymer blocks (b), the total of the number-average degrees of polymerization of the respective vinyl alcohol-based polymer blocks (b) is defined as the number-average molecular weight ($Mn_b$). The $Mn_b$ of 15,000 or more allows improvement of the gel shape retentivity while maintaining the absorbency. The $Mn_b$ is preferably 20,000 or more, more preferably 30,000 or more, even more preferably 35,000 or more, and particularly preferably 40,000 or more. Meanwhile, an $Mn_b$ of more than 220,000 causes a decrease in the absorbency. The $Mn_b$ is preferably 180,000 or less, more preferably 150,000 or less, and even more preferably 120,000 or less. The $Mn_b$ is determined by performing GPC measurement and, as needed, $^1$H-NMR measurement of the polymer sampled from the reaction liquid during the polymerization, and then calculating the $Mn_b$ from the obtained number-average molecular weight and the obtained contents of respective monomer units of the polymer, and specifically, the method described in Examples described later is adopted.

The ratio ($Mn_b/Mn_A$) of the number-average molecular weight ($Mn_b$) of the vinyl alcohol-based polymer block (b)

to the number-average molecular weight ($Mn_A$) of the block copolymer (A) is from 0.1 to 0.9. The ratio ($Mn_b/Mn_A$) of 0.1 or more causes the block copolymer (A) to have improved gel shape retentivity and water solubility. The ratio ($Mn_b/Mn_A$) is preferably 0.2 or more and more preferably 0.3 or more. Meanwhile, the ratio ($Mn_b/Mn_A$) of 0.9 or less causes the block copolymer (A) to have improved absorbency. The ratio ($Mn_b/Mn_A$) is preferably 0.8 or less and more preferably 0.7 or less.

The block copolymer (A) of the present invention preferably has a molecular weight distribution ($Mw_A/Mn_A$) from 1.05 to 1.95. Polymerization by controlled radical polymerization allows production of the block copolymer (A) having a narrow molecular weight distribution. The molecular weight distribution ($Mw_A/Mn_A$) is preferably 1.80 or less, more preferably 1.65 or less, and even more preferably 1.55 or less. The molecular weight distribution ($Mw_A/Mn_A$) within the above range causes the block (b) and the block (c) to form a compact phase separation structure, leading to improvement of the absorbency and the shape retentivity.

In the polymerization step, polymerization of the monomer containing the vinyl ester monomer and polymerization of the monomer containing the ionic monomer and the vinyl ester monomer are performed to obtain the vinyl ester-based block copolymer comprising the vinyl ester polymer block (b1) and the ionic polymer block (c1). In a preferred embodiment, the vinyl ester-based block copolymer is subjected to the saponification step and the optional salt formation step to obtain the block copolymer (A) comprising: the vinyl alcohol-based polymer block (b); and the ionic polymer block (c) containing the monomer unit with the ionic group forming a salt and the vinyl alcohol-based monomer unit.

When (meth)acrylic acid or a (meth)acrylic ester is used as the ionic monomer, a polymer obtained by heat-treating the block copolymer (A) in an acidic aqueous solution and then drying the block copolymer preferably has a molar ratio ($V_A$) of the lactone ring to the total of the acrylic acid monomer units and the lactone ring [lactone ring/total of acrylic acid monomer units and lactone ring] of 0.75 or more.

The heat treatment of the block copolymer (A) in an acidic aqueous solution causes an acrylic acid monomer unit adjacent to the vinyl alcohol monomer unit and capable of forming a lactone ring with the vinyl alcohol monomer unit to be converted to a lactone ring. Meanwhile, in the case where acrylic acid monomer units are continuous, a lactone ring is not formed and remains as an acrylic acid monomer unit even when the treatment is performed. Accordingly, when the proportion of the portion in which the vinyl alcohol monomer unit and the acrylic acid monomer unit are alternately arranged is large, that is, when the proportion of the portion in which the acrylic acid ester monomer unit and the acrylic acid monomer unit are continuous is small, the molar ratio ($V_A$) [lactone ring/total of acrylic acid monomer units and lactone ring] is high. That is, the molar ratio ($V_A$) [lactone ring/total of acrylic acid monomer units and lactone ring] is an index of the randomness of the ionic polymer block (c) containing the vinyl alcohol-based monomer unit and the acrylic acid monomer unit forming a salt. The molar ratio ($V_A$) [lactone ring/total of acrylic acid monomer units and lactone ring] of 0.75 or more causes the block copolymer (A) to have further improved gel shape retentivity. The molar ratio ($V_A$) [lactone ring/total of acrylic acid monomer units and lactone ring] is more preferably 0.80 or more, even more preferably 0.85 or more, and particularly preferably 0.90 or more. As the conditions for the heat treatment and drying of the block copolymer (A), the conditions described in Examples are employed.

A polymer obtained by re-saponifying the block copolymer (A) to a degree of saponification of 99 mol % or more preferably has a crystalline melting temperature ($Q_A$) [° C.] of 210° C. or more. The block copolymer (A) thus having a relatively high crystalline melting temperature ($Q_A$) allows further improvement of the gel shape retentivity. The $Q_A$ is more preferably 215° C. or more and even more preferably 220° C. or more. The $Q_A$ can be measured by the method described in Examples.

It is preferable that an amount of deionized water absorbed per 0.1 g of the block copolymer (A) at 20° C. is 20 g or more. Although there is no particular upper limit, the amount is usually less than 100 g. It is also preferable that an amount of a 0.9 mass % aqueous sodium chloride solution absorbed per 1 g of the block copolymer (A) at 20° C. is 20 g or more. Although there is no particular upper limit, the amount is usually less than 100 g. The amounts of the absorbed deionized water and the absorbed aqueous sodium chloride solution are measured by the method described in Examples. The block copolymer (A) thus having high absorbency of deionized water and salt water is preferably used for various applications.

It is preferable that, when 1 g of the block copolymer (A) is dissolved in 1000 ml of water at 95° C., a soluble amount is 95 mass % or more. It is more preferable that, when the block copolymer (A) is dissolved in 1000 ml of water at 20° C., a soluble amount is 95 mass % or more. The block copolymer (A) thus also having high solubility in water is environmentally excellent. In addition, the block copolymer (A) after absorbing water, salt water, and the like can be discharged into the sewage, allowing waste reduction. Moreover, it is considered that new applications can be developed using the performance of such a block copolymer (A). The soluble amount is calculated the method described in Examples.

It is preferable that the block copolymer (A) is highly biodegradable. The high biodegradability achieves excellent environmental properties. In addition, both the large soluble amount when dissolved in water and the high biodegradability rate described above allow even more waste reduction of the block copolymer (A). The biodegradation rate is preferably 20% or more and more preferably 40% or more. The biodegradation rate can be obtained by the method described in Examples.

It is possible to appropriately change the absorbency and the water solubility of the block copolymer (A) of the present invention by designing the block copolymer (A). For example, given that the amount of deionized water absorbed per 0.1 g is $X_{DIW}$[g], the soluble amount when 1 g of the block copolymer (A) is dissolved in 1000 ml of water at 95° C. is $Y_{95}$[mass %], the soluble amount when 1 g of the block copolymer (A) is dissolved in 1000 ml of water at 20° C. is $Y_{20}$[mass %], it is possible to prepare the block copolymer (A), such as: a copolymer with $X_{DIW}$ of 20 or more, $Y_{95}$ of 95 or more, and $Y_{20}$ of 95 or more; a copolymer with $X_{DIW}$ of 20 or more, $Y_{95}$ of 95 or more, and $Y_{20}$ of 0 or more and 95 or less; a copolymer with $X_{DIW}$ of 40 or more, $Y_{95}$ of 95 or more, and $Y_{20}$ of 95 or more; and a copolymer with $X_{DIW}$ of 40 or more, $Y_{95}$ of 95 or more, and $Y_{20}$ of 0 or more and 95 or less. In addition, depending on the applications, the soluble amount in water may be adjusted in a temperature range other than 95° C. and 20° C. described above.

An absorber comprising the block copolymer (A) is a preferred embodiment of the present invention. The form of the absorber is not particularly limited, and examples of the form include particles, sheets, tapes, gels, ointments, films, fibers, and the like. Among them, the form of particles is preferred. The content of the block copolymer (A) in the absorber is not particularly limited, and is preferably 1 mass % or more, more preferably 5 mass % or more, and even more preferably 10 mass % or more.

As the components other than the block copolymer (A) in the absorber, materials that prevents falling of the block copolymer (A) and do not inhibit liquid permeation are appropriately used. Examples of such a component include paper and pulp, such as tissue paper, various types of nonwoven fabric (spunbonded nonwoven fabric, meltblown nonwoven fabric, thermally bonded nonwoven fabric, needle punched nonwoven fabric, spunlace nonwoven fabric, airlaid nonwoven fabric, etc.), and the like. They may be subjected to, as needed, water solubility providing treatment, hydrolysis treatment, hydrophilization treatment, and aperture providing treatment. These components may be polymers, such as a polyvinyl alcohol, polyacrylic acid, polyacrylamide, polyurethane, polylactic acid, starch, cellulose, polyoxyalkylene, polyethylene, polypropylene, and polyethylene terephthalate, to be used alone or in combination.

An absorbent article comprising the absorber is a more preferred embodiment. The absorbent article is preferably used for sanitary, commodity, construction, civil engineering, industrial, agricultural, medical, food applications, and the like. Specifically, the absorbent article is preferably used as an absorbent article for: sanitary applications, such as disposable diapers, diaper pads, sanitary napkins, nursing pads, incontinence pads, sweat absorbent bands, and water-soluble sanitary materials; commodity applications, such as gel air fresheners, disposable heating pad materials, cat litter, pet sheets, deodorants, and portable toilets; construction and civil engineering applications, such as drip absorbents, sealing compounds, sealing compounds for curing concrete, lost circulation preventing materials, water loss preventing materials, sealants, and desert greening materials; other industrial applications, such as antisweat sheets for containers, fire extinguishers, watertight materials for communication cables, alkaline battery materials, water swelling paints, water wetting paints, artificial snow compounds, and water removing agents for oil; agricultural applications, such as soil water retention agents, seedling raising sheets, seed coatings, slow release agents for fertilizers, and disintegration aids for pesticides and fertilizers; medical applications, such as moisturizers, dressing materials for wound protection, waste blood solidifiers, underpads for medical applications, cataplasms, and body fluid absorbers; food applications, such as ice packs and freshness keeping agents; and the like. Such an absorbent article having the absorber composed of water-soluble and hydrolytic components after absorbing body fluid, for example, allows the absorbent article itself or an absorber portion detached from the absorbent article to be readily disposed of in water. Accordingly, the absorbent article is preferably used as a sanitary material allowed to be thrown in flushing water without pretreatment, such as grinding. Use of the block copolymer (A) excellent in biodegradability allows decomposition in activated sludge and thus allows disposal in the sewage. The use also allows release control of the absorber having absorbed and retained the components, such as a detergent, an agricultural chemical, and a fertilizer, using the amount of water as a trigger.

EXAMPLES

With reference to Examples, the present invention will be described below more specifically.

[Materials Used in Examples]

Cobalt(II) acetylacetonate $(Co(acac)_2)$
    Cobalt(II) tetramesitylporphyrin (Co(TMP))
    [2,2'-azobis(4-methoxy-2,4-dimethylvaleronitrile)] (V-70)
    Azobisisobutyronitrile (AIBN)
    Vinyl acetate (VAc)
    Methyl acrylate (MA)
    2-acrylamide-2-methylpropanesulfonic acid (AMPS)
    3-(methacrylamide)propyl trimethylammonium chloride (MAPTAC)
    1,1-diphenylethylene (1,1-DPEt)

[Number-Average Molecular Weight $(Mn_A)$, Number-Average Molecular Weight $(Mn_b)$, and Molecular Weight Distribution $(Mw_A/Mn_A)$]

The number-average molecular weight (Mn) and the molecular weight distribution (Mw/Mn) of the polymer were measured using a gel permeation chromatograph manufactured by Shimadzu Corp. Measurement conditions were as follows.

Column: two tetrahydrofuran-based columns "KF-806M" manufactured by Showa Denko K.K., serial connection
    Reference material: polymethylmethacrylate
    Solvent and mobile phase: tetrahydrofuran (THF)
    Flow rate: 1.0 mL/min.
    Temperature: 40° C.
    Sample solution concentration: 0.2 mass % (filtered through a filter having an opening diameter of 0.45 $\mu$m)
    Injection amount: 100 $\mu$L Detector: RI

[Content (U) of Ionic Monomer Unit in Vinyl Ester-Based Block Copolymer]

The content (U) (mol %) of the acrylic acid ester monomer unit (ionic monomer unit) in the vinyl ester-based block copolymer was determined by the following method. $^1$H-NMR measurement of the vinyl ester-based block copolymer was performed. The content (U) (mol %) of the acrylic acid ester monomer unit in the vinyl ester-based block copolymer was calculated by the following formula, where T was the integral value (4.8 ppm) of the peak derived from the methine proton $(-CH_2CH(OCOCH_3)-)$ of the vinyl acetate monomer unit, and S was the integral value (3.6 ppm) of the peak derived from the side chain protons $(-CH_2CH(COOCH_3)-)$ of the methyl acrylate monomer unit.

$$(U) \text{ (mol \%)} = (S/3)/(S/3+T) \times 100$$

In the case of using MAPTAC as the ionic monomer, the content (U) (mol %) of the MAPTAC monomer unit in the vinyl ester-based block copolymer was calculated by the following formula, where S' was the integral value (peak detected in the range from 3.1 to 3.3 ppm) of the peak derived from the N-methyl proton $(-N(CH_3)_3)$.

$$(U) \text{ (mol \%)} = (S'/9)/(S'/9+T) \times 100$$

In the case of using AMPS instead of the acrylic ester monomer, the content (U) (mol %) of the AMPS monomer unit in the vinyl ester-based block copolymer was calculated by the following formula, where S'' was the integral value (peak detected in the range from 2.9 to 3.2 ppm) of the peak derived from the side chain methylene proton $(-CH_2SO_3H)$.

$$(U) \text{ (mol \%)} = (S''/2)/(S''/2+T) \times 100$$

[Number-Average Degree of Polymerization $DP_A$ of Block Copolymer (A) and Number-Average Degree of Polymerization $DP_b$ of Polymer Block (b)]

The number-average degree of polymerization $DP_b$ of the polymer block (b) in the copolymer (A) was determined as follows.

The polymer block (b) is formed by saponifying the vinyl ester polymer block (b1) in the vinyl ester-based block copolymer. Since the number-average degree of polymerization $DP_b$ of the polymer substantially does not change before and after the saponification, the number-average degree of polymerization determined from the results of the GPC measurement of the polymer before saponification was defined as the number-average degree of polymerization $DP_b$ of the polymer block (b). Similarly, after the polymerization was terminated, the number-average degree of polymerization determined from the results of the GPC measurement of the polymer before saponification was defined as the number-average degree of polymerization $DP_A$ of the copolymer (A).

In this context, the vinyl ester polymer block (b1) refers to a block (b1) obtained by polymerizing a vinyl ester in the absence of the ionic monomer, such as an acrylic acid ester and to a block (b1) obtained by polymerizing a vinyl ester in the presence of the ionic monomer at the initial stage of polymerization or during polymerization to obtain a copolymer block (c1) containing a vinyl ester monomer unit and an ionic monomer unit, and then polymerizing the vinyl ester-based monomer in a state where the ionic monomer was consumed earlier than the vinyl ester and the molar ratio of the ionic monomer to the vinyl ester in the reaction liquid (ionic monomer/vinyl ester) was 0.00001 or less.

The boundary between the "vinyl ester polymer block (b1)" and the "copolymer block (c1) containing a vinyl ester-based monomer unit and an ionic monomer unit" was determined as follows. Sampling was appropriately performed during the polymerization, the number-average degree of polymerization (DP) of the polymer and the content (U) (mol %) of the ionic monomer unit at the time point of each sampling were measured by GPC and $^1$H-NMR, and the time point when the molar ratio (ionic monomer/vinyl ester) reached 0.00001 was determined by simulation using the Mayo-Lewis formula as a copolymerization theoretical formula and the value of the reactivity ratio $(r_{VAc}=0.01, r_{MA}=30)$. In this situation, the content of the ionic monomer unit contained in the vinyl ester polymer block (b1) formed in a state in which the molar ratio (ionic monomer/vinyl ester) reached 0.00001 or less was less than 0.1 mol %.

The number-average degree of polymerization (DP) of the sampled polymer was determined by the following formula using the number-average molecular weight Mn of the polymer and the content (U) (mol %) of the acrylic acid-based monomer unit, determined by GPC and $^1$H-NMR, and the molecular weights of the acrylic acid ester monomer unit and the vinyl ester monomer unit (MA: 86, VAc: 86).

$$(DP) = Mn/\{(U/100) \times 86 + [(100-U)/100] \times 86\}$$

The number-average degree of polymerization $DP_A$ of the copolymer (A) was determined from the above formula using values determined by GPC and $^1$H-NMR of the vinyl ester-based block copolymer after the polymerization was terminated. In the case of obtaining a vinyl ester-based polymer block at the beginning of polymerization, the polymer sampled immediately before adding the ionic monomer was measured to determine the number-average degree of polymerization $DP_b$ of the polymer block (b). In the case of obtaining a vinyl ester-based polymer block after performing copolymerization of an acrylic acid ester and a vinyl ester, the number-average degree of polymerization $DP_b$ of the polymer block (b) was determined from the difference in number-average polymerization degree obtained by measuring the polymer sampled at the time point of the boundary of blocks and the vinyl ester-based block copolymer after the polymerization was terminated.

[Content ($Z_A$) (mol %) of Unit Derived from Ionic Monomer in Block Copolymer (A)]

In the case of using an acrylic ester as the ionic monomer, the obtained copolymer (A) was stirred at 100° C. for 1 hour in an aqueous hydrochloric acid solution of pH 2 and then dried and solidified at 120° C., and thereby all acrylic acid-based monomer units (acrylic acid units, acrylic ester units, acrylate units) in the copolymer were converted to acrylic acid monomer units or lactone ring structures (the lactone ring was formed through a reaction of an acrylic acid monomer unit or an acrylic acid ester monomer unit with a vinyl alcohol monomer unit adjacent thereto). The copolymer was washed with methanol to remove salts, then dried under reduced pressure at 90° C. for 2 days. The polymer was thus obtained by heat treatment in the acidic aqueous solution and then drying. The copolymer (polymer obtained by heat treatment in the acidic aqueous solution and then drying) was subjected to $^1$H-NMR measurement at 40° C. and 95° C. using a nuclear magnetic resonance spectrometer "LAMBDA 500" manufactured by JEOL Ltd. DMSO-$d_6$ was used as a solvent. The content ($Z_A$) (mol %) of the acrylic acid-based monomer unit based on the total monomer units of the copolymer (A) was calculated as follows.

The content ($Z_A$) (mol %) of the acrylic acid-based monomer unit based on the total monomer units of the copolymer (A) was calculated by the following formula.

$$(Z_A) \text{ (mol \%)}=(X+Y)/(W+2X+Y+(P/3))\times100$$

In the formula, each symbol means as follows.

Y: integral value (broad peak detected in the range from 11.0 to 13.0 ppm) of a peak derived from a side chain proton (—$CH_2CH(COOH)$—) of acrylic acid X: total integral value (double peak from 2.6 ppm to 3.0 ppm) of a peak derived from a methine proton (—$CH_2\underline{CH}(R_1)CH_2CH(R_2)$—) of the main chain of acrylic acid in the lactone ring, wherein $R_1$—$R_2$ forms a bond with each other and —$R_1$—$R_2$— means a —CO—O— structure W: total integral value (a peak from 3.6 ppm to 4.0 ppm) of a peak derived from a methine proton (—$CH_2CH$ (OH)—) of the vinyl alcohol P: integral value (1.9 ppm to 2.0 ppm) of a peak derived from side chain protons (—$CH_2CH(OCOCH_3)$—) of vinyl acetate In the case of using MAPTAC instead of the acrylic ester monomer, the content ($Z_A$) (mol %) of the MAPTAC monomer unit in the copolymer (A) was calculated by the following formula using P and W above, wherein F2 denotes the integral value (a peak detected in the range from 3.1 to 3.3 ppm) of a peak derived from the N-methyl proton (—$N(\underline{CH}_3)_3$). In the case of using AMPS instead of the acrylic ester monomer, the content ($Z_A$) (mol %) of the AMPS monomer unit in the copolymer (A) was calculated by the following formula using P and W above, wherein F3 denotes the integral value (a peak detected in the range from 2.9 to 3.2 ppm) of a peak derived from the side chain methylene proton (—$C\underline{H}_2SO_3H$).

$$(Z_A) \text{ (mol \%)}=(F2/9)/((F2/9)+W+(P/3))\times100$$

$$(Z_A) \text{ (mol \%)}=(F3/2)/((F3/2)+W+(P/3))\times100$$

[Molar Ratio ($V_A$) of Lactone Ring [Lactone Ring/Total of Acrylic Acid Monomer Units and Lactone Ring]]

The molar ratio ($V_A$) of the lactone ring to the total of the acrylic acid monomer units and the lactone ring [the lactone ring/the total of the acrylic acid monomer units and the lactone ring] in the polymer (polymer obtained by heat treatment in the acidic aqueous solution and then drying) was calculated by the following formula using X and Y above.

$$(V_A)=X/(X+Y)$$

[Content ($R_c$) of Unit Derived from Ionic Monomer in Polymer Block (c)]

The content ($R_c$) (mol %) of the acrylic acid-based monomer unit based on the total monomer units in the polymer block (c) containing the vinyl alcohol-based monomer unit and the acrylic acid-based monomer unit in the copolymer (A) was calculated by the following formula using the number-average degree of polymerization $DP_A$ of the copolymer (A) and the number-average degree of polymerization $DP_b$ of the polymer block (b).

$$(R_c) \text{ (mol \%)}=(Z_A)\times DP_A/(DP_A-DP_b)$$

[Content ($H_c$) of Unit Derived from Vinyl Alcohol-Based Monomer in Polymer Block (c)]

The content ($H_c$) (mol %) of the vinyl alcohol-based monomer unit based on the total monomer units in the polymer block (c) containing the vinyl alcohol-based monomer unit and the acrylic acid-based monomer unit in the copolymer (A) was calculated by the following formula.

$$(H_c) \text{ (mol \%)}=100-(R_c)$$

[Degree of Saponification]

The degree of saponification (mol %) of the copolymer (A) was calculated by the following formula using P and W above.

$$\text{Degree of Saponification (mol \%)}=1-(P/3)/(W+(P/3))\times100$$

[Content ($J_A$) of Monomer Unit with Ionic Group Forming Salt in Block Copolymer (A)]

The content ($J_A$) of the monomer unit with the ionic group forming a salt based on the total monomer units in the copolymer (A) was calculated by the following formula using, for example, W, X, Y, P, and an integral value F1 (a peak detected in the range from 2.4 to 2.7 ppm) of a peak derived from the methine proton (—$CH_2\underline{CH}(COOM)$-) of acrylate, which were detected by $^1$H-NMR measurement of the copolymer (A). In this context, M denotes a counteration of acrylate.

$$(J_A) \text{ (mol \%)}=F1/(F1+W+2X+Y+(P/3))\times100$$

In the case of using AMPS or AMPS instead of the acrylic ester monomer, the content was calculated by the following formula using W, P, F2, and F3 above.

$$(J_A) \text{ (mol \%)}=(F2/9)/((F2/9)+W+(P/3))\times100$$

$$(J_A) \text{ (mol \%)}=(F3/2)/((F3/2)+W+(P/3))\times100$$

[Content ($K_c$) of Monomer Unit with Ionic Group Forming Salt in Ionic Polymer Block (c)]

The content ($K_c$) of the ionic monomer unit forming a salt in the polymer block (c) was calculated by the following formula.

$$(K_c) \text{ (mol \%)}=(J_A)\times DP_A/(DP_A-DP_b)$$

[Crystal Melting Temperature ($Q_A$)]

To 100 parts by mass of the copolymer (A), 1860 parts by mass of methanol and 50 parts by mass of sodium hydroxide were added, and the mixture was heated at 40° C. for 2 hours to completely saponify the remaining acetic acid groups (degree of saponification 99.9 mol %). When the saponification was insufficient, additional sodium hydroxide was added to continue the reaction until the remaining acetic acid groups were completely saponified. Next, a phenolphthalein solution was added, and the reaction mixture was washed with methanol until no alkaline reaction was observed in the washing liquid (methanol), and then sodium hydroxide and sodium acetate were removed. The washed polymer was dried up at 120° C. until methanol disappeared, thereby affording a polymer for crystal melting temperature measurement.

The crystal melting temperature ($Q_A$) of the polymer under a nitrogen atmosphere was measured using a differential scanning calorimeter "DSC 25" manufactured by TA Instruments. The polymer (3 mg) dried under reduced pressure at 90° C. for 2 days was sealed in an aluminum container and set in the differential scanning calorimeter. The temperature was raised from 40° C. to 250° C. at a rate of 10° C. per minute, then held for 1 minute, then lowered to minus 80° C. at a rate of 10° C. per minute, and then held for 1 minute. Thereafter, the temperature was raised to 250° C. at a rate of 10° C. per minute, and during this course, an endothermic peak was observed between 150° C. and 250° C. The temperature of the local maximum point on the peak was defined as ($Q_A$) (° C.).

[Evaluation of Deionized Water (DIW) Absorbency of Block Copolymer (A)]

In a 100 mL beaker, 0.1 g of the copolymer (A) was placed, and under an atmosphere at 20° C., 10, 20, 30, 40, 50, or 60 g of deionized water was gently added to the beaker and left still for 10 minutes. Immediately after that, the contents in the beaker were moved on a mesh with a pore size of 74 μm. In the case that no water droplets were dripped from the mesh within 1 minute, a determination was made that the total amount was absorbed to determine the maximum amount of deionized water allowed for total amount absorption [deionized water (g)/copolymer (A) (g)] and evaluate the value as the "absorbency".

[Evaluation of Salt Water (Saline) Absorbency and Retentivity of Block Copolymer (A)]

In a 100 mL beaker, 1 g of the copolymer (A) was placed, and under an atmosphere at 20° C., 10, 20, 30, 40, 50, or 60 g of an aqueous sodium chloride solution with a concentration of 0.9 mass % was gently added to the beaker and left still for 10 minutes. Immediately after that, the contents in the beaker were moved on a mesh with a pore size of 74 μm. In the case that no water droplets were dripped from the mesh within 1 minute, a determination was made that the total amount was absorbed to determine the maximum amount of the aqueous solution allowed for total amount absorption [aqueous solution (g)/copolymer (A) (g)] and evaluate the value as the "absorbency". In addition, after the leaving still for 10 minutes, the beaker was turned sideways and left still to evaluate the maximum amount of the aqueous solution keeping the contents from leaking out of the beaker [aqueous solution (g)/copolymer (A) (g)] as the "retentivity".

[Evaluation of Soluble Amount of Block Copolymer (A) in Deionized Water (DIW)]

To 1000 ml of deionized water, 1 g of the copolymer (A) was added and stirred under an atmosphere at 20° C. or at 95° C. for 60 minutes, and then filtered through a 200-mesh metal sieve. The residue on the sieve was heated and dried at 120° C. for 4 hours to define the resulting mass as D (g). A soluble amount E (ratio of dissolution in water) as an index of the water solubility was calculated by the following formula.

$$E \text{ (mass \%)} = (1-D) \times 100$$

[Evaluation of Biodegradation Rate of Block Copolymer (A)]

In accordance with JIS K 6951, 20 mg of the copolymer (A) was added to 200 ml of standard test culture medium where 8.5 g of potassium dihydrogen phosphate anhydrous, 21.75 g of dipotassium hydrogen phosphate anhydrous, 33.4 g of disodium hydrogen phosphate, and 0.5 g of ammonium chloride were dissolved in 1000 ml of distilled water, and then standard activated sludge was added to 20 ppm. The culture medium was cultured at 22° C. for 28 days while stirring. Then amount of carbon dioxide generated in this period was periodically measured to determine the total amount F (mg) of the generated carbon dioxide. The total amount G (mg) of carbon dioxide generated from a culture medium in which the copolymer (A) was not added was similarly determined. In addition, a calculated value H (mg) of the amount of carbon dioxide generated during complete decomposition of the copolymer (A) was determined to obtain the biodegradation rate (%) by the following formula.

$$\text{Biodegradation Rate (\%)} = \{(F-G)/H\} \times 100$$

Example 1

Polymerization Step

[Synthesis of Block b]

To a reactor provided with a stirrer, a reflux condenser tube, and an initiator inlet port, 0.19 parts by mass of Co(acac)$_2$ and 0.67 parts by mass of V-70 as an initiator were added. Inert gas purge was performed three times in which the inside of the reactor was vacuumed and then nitrogen was introduced. After that, 500 parts by mass of VAc purified by simple distillation was added, followed by immersion of the reactor in a water bath and heating to have an internal temperature of 30° C. and stirring.

[Synthesis of Block c]

While stirring, sampling was appropriately performed and the progress of the polymerization was checked from the solid concentration. When the conversion of VAc reached 19 mass %, 7.8 parts by mass of MA was added (corresponding to "Addition All at Once" of Additional Monomer in Table 1). The number-average molecular weight (Mn) of the polymer at the conversion of 19 mass % was 129,000. Subsequently, sampling was appropriately performed and the progress of the polymerization was checked from the solid concentration, and when the total conversion of VAc and MA reached 26 mass %, the complete consumption of MA [molar ratio (acrylic ester/vinyl ester) of less than 0.00001] was checked by $^1$H-NMR and 0.66 parts by mass of 1,1-DPEt was added as a polymerization inhibitor. In this situation, the number-average molecular weight (Mn) was 182,600.

While the block b was produced, the induction period of the polymerization was 6 hours and the growth period from the start of increasing the degree of polymerization to the addition of the polymerization inhibitor was 4 hours.

[Purification of Block Copolymer]

After the addition of the polymerization inhibitor, the internal temperature was raised to 60° C., followed by heating and mixing for 1 hour, and 500 parts by mass of an aqueous acetic acid solution (pH of 2.0) with a concentration of 25 mass % was further added thereto and stirred for 5 minutes. Thereafter, the mixture was left standing for 30 minutes to be separated into two layers, and the aqueous layer was removed. The reactor was connected to a vacuum line, and unreacted monomers were distilled off under reduced pressure at 30° C., then methanol was added to dissolve the vinyl ester-based block copolymer, and the solution was added dropwise to deionized water to precipitate the vinyl ester-based block copolymer. The vinyl ester-based block copolymer was collected by filtration operation and dried in a vacuum dryer at 40° C. for 24 hours to obtain the vinyl ester-based block copolymer. Details of the above polymerization step are shown in Table 1.

Saponification Step

Then, to a reactor same as above, 100 parts by mass of the vinyl ester-based block copolymer thus obtained and 1833.6 parts by mass of dehydrated methanol were added and dissolved, and then the water bath was heated and the solution was heated and stirred until the internal temperature reached 40° C. Thereto, 66.4 parts by mass of a methanol solution of sodium hydroxide (concentration of 14 mass %, 9.3 parts by mass as sodium hydroxide) was added. The vinyl ester-based block copolymer solution thus prepared having a concentration of 5 mass % was subjected to saponification reaction at 65° C. for 1 hour.

Salt Formation Step

To the saponified product obtained by deliquoring, 46.5 parts by mass of sodium hydroxide, 2000 parts by mass of dehydrated methanol, and 210 parts by mass of ion exchanged water were added, and heating was further continued at 65° C. for 1 hour. After deliquoring, a phenolphthalein solution was added to the washing liquid (methanol) and the deliquored material was washed with methanol until no alkaline reaction was observed to remove sodium hydroxide and sodium acetate. The solid obtained by centrifugal dewatering was dried in a vacuum dryer at 40° C. for 24 hours to obtain the intended copolymer (A) (binary block copolymer of block (b)-block (c)).

Properties of Block Copolymer (A)

Various properties of the copolymer (A) thus obtained were measured to evaluate the performance. The copolymer (A) had a number-average molecular weight ($Mn_A$) of 99,800, and the polymer block (b) in the copolymer (A) had a number-average molecular weight ($Mn_b$) of 66,100. The ratio ($Mn_b/Mn_A$) was 0.66, the molecular weight distribution ($Mw_A/Mn_A$) was 1.30, and the degree of saponification was 99.9 mol %. The above results are summarized in Table 2.

Example 2

The copolymer (A) (binary block copolymer of block b-block c) was obtained in the same manner as that in Example 1 other than changing the [Synthesis of Block c] of Polymerization Step in Example 1 as shown in Table 1. The evaluation results of the copolymer (A) thus obtained are shown in Table 2.

Example 3

Polymerization Step

[Synthesis of Block b]

To a reactor provided with a stirrer, a reflux condenser tube, an initiator inlet port, and a feed pump, 0.19 parts by mass of Co(acac)$_2$ and 0.67 parts by mass of V-70 as an initiator were added. Inert gas purge was performed three times in which the inside of the reactor was vacuumed and then nitrogen was introduced. After that, 500 parts by mass of VAc purified by simple distillation was added, followed by immersion of the reactor in a water bath and heating to have an internal temperature of 30° C. and stirring.

[Synthesis of Block c]

While stirring, sampling was appropriately performed and the progress of the polymerization was checked from the solid concentration. When the conversion of VAc reached 13 mass %, 1.3 parts by mass of MA was added (corresponding to "Addition All at Once" of Additional Monomer in Table 1). The number-average molecular weight (Mn) of the polymer at the conversion of 13 mass % was 86,000. Immediately after that, polymerization was performed while a mixture of 25 parts by mass of VAc and 6.2 parts by mass of MA was fed with time. The progress of the polymerization was checked from the solid concentration and the sampled polymer was also subjected to GPC measurement and $^1$H-NMR measurement, and when the total conversion of VAc and MA reached 18 mass %, the feed was completed (corresponding to Feed in Table 1).

Then, at the time point when the total conversion of VAc and MA was 22%, the complete consumption of MA [molar ratio (acrylic ester/vinyl ester) of less than 0.00001] was checked by $^1$H-NMR. In this situation, the number-average molecular weight (Mn) was 161,700. When the total conversion of VAc and MA reached 22 mass %, 0.66 parts by mass of 1,1-DPEt was added as a polymerization inhibitor.

While the block b was produced, the induction period of the polymerization was 6 hours and the growth period from the start of increasing the degree of polymerization to the addition of the polymerization inhibitor was 3 hours.

[Purification of Block Copolymer]

Then, purification was performed by the same method as that in Example 1 to obtain a vinyl ester-based block copolymer. Details of the above polymerization step are shown in Table 1.

Saponification Step and Salt Formation Step

Subsequently, the saponification step and the salt formation step were performed by the same methods as in Example 1 to obtain the intended copolymer (A) (binary block copolymer of block b-block c). The results of measuring and evaluating the copolymer (A) thus obtained are summarized in Table 2.

Example 4

The copolymer (A) (binary block copolymer of block b-block c) was obtained in the same manner as that in Example 3 other than changing the [Synthesis of Block c] of Polymerization Step in Example 3 as shown in Table 1. The evaluation results of the copolymer (A) thus obtained are shown in Table 2.

Example 5

The intended copolymer (A) (binary block copolymer of block b-block c) was obtained in the same manner as that in Example 3 other than changing the [Synthesis of Block c] of Polymerization Step in Example 3 as shown in Table 1. The evaluation results of the copolymer (A) thus obtained are shown in Table 2.

Example 6

The intended copolymer was obtained in the same manner as that in Example 3 other than changing the [Synthesis of Block b] and [Synthesis of Block c] of Polymerization Step in Example 3 as shown in Table 1. The evaluation results of the copolymer thus obtained are shown in Table 2.

It should be noted that, in Example 6, the polymerization was continuously performed even after complete consumption of MA in the comonomer in the procedure corresponding to [Synthesis of Block c] and then the polymerization terminator was added. Accordingly, the finally obtained copolymer has a triblock structure of block b-block c-block b.

Example 7

The intended copolymer (A) (binary block copolymer of block b-block c) was obtained in the same manner as that in Example 1 other than using 46.5 parts by mass of calcium hydroxide instead of 46.5 parts by mass of sodium hydroxide in Saponification Step in Example 1 as shown in Table 1. The evaluation results of the copolymer thus obtained are shown in Table 2.

Specific changes were made as follows. Instead of the procedure in which "to the saponified product obtained by deliquoring, 46.5 parts by mass of sodium hydroxide, 2000 parts by mass of dehydrated methanol, and 210 parts by mass of ion exchanged water were added", the procedure was performed in which "to the saponified product obtained by deliquoring, 46.5 parts by mass of calcium hydroxide, 2000 parts by mass of dehydrated methanol, and 210 parts by mass of ion exchanged water were added".

It should be noted that the procedure in which "66.4 parts by mass of a methanol solution of sodium hydroxide (concentration of 14 mass %, 9.3 parts by mass as sodium hydroxide) was added" was performed in the same manner as that in Example 1.

Comparative Example 1

Polymerization Step
[Synthesis of Random Copolymer]

In a reactor provided with a stirrer, a reflux condenser tube, an argon inlet tube, an initiator inlet port, and a feed pump, 640 parts by mass of VAc, 1.1 parts by mass of MA (corresponding to Initial Monomer in Table 1), and 250 parts by mass of methanol were charged, and the inside of the reactor was purged with an inert gas for 30 minutes while bubbling nitrogen. A water bath was heated to start warming of the reactor, and when the internal temperature reached 60° C., 0.15 part by mass of AIBN was added as an initiator to initiate polymerization.

Polymerization was performed while a 40 mass % methanol solution of MA was fed with time. Sampling was appropriately performed and the progress of the polymerization was checked from the solid concentration, and when the total conversion of VAc and MA reached 35 mass %, 0.15 parts by mass of p-benzoquinone was added to terminate the polymerization. The total amount of MA fed at this time point was equivalent to 11.4 parts by mass (corresponding to Additional Monomer in Table 1).

While the block c was produced, the induction period of the polymerization was 0 hours and the growth period from the start of increasing the degree of polymerization to the addition of the polymerization inhibitor was 3 hours.

Subsequently, purification, saponification, and salt formation were performed by the same methods as in Example 1 to obtain the intended random copolymer. The evaluation results of the copolymer thus obtained are shown in Table 2.

Comparative Example 2

The saponification step in Example 3 was changed as follows. To 100 parts by mass of the vinyl ester-based block copolymer obtained in Polymerization Step in Example 3, 46.5 parts by mass of acetic acid and 2000 parts by mass of methanol were added and heated at 65° C. for 1 hour. After deliquoring, the deliquored material was washed with methanol and the solid obtained by centrifugal dewatering was dried in a vacuum dryer at 40° C. for 24 hours to obtain the intended block copolymer. The Salt Formation Step was not performed. The results of measuring and evaluating the block copolymer thus obtained are summarized in Table 2.

Comparative Example 3

A copolymer (A) (binary block copolymer of block b-block c) was obtained in the same manner as that in Example 1 other than changing the [Synthesis of Block b] and [Synthesis of Block c] in Polymerization Step in Example 1 as shown in Table 1. The evaluation results of the copolymer (A) thus obtained are shown in Table 2.

Comparative Example 4

A chemically crosslinked polyacrylic acid-based superabsorbent resin (trade name: AQUA KEEP SA60S, produced by Sumitomo Seika Chemicals Co., Ltd.) was used for evaluation and the results are summarized in Table 2.

Comparative Example 5

Polymerization Step
[Synthesis of Block c]

To a reactor provided with a stirrer, a reflux condenser tube, and an initiator inlet port, 1.56 parts by mass of Co(TMP) and 0.91 parts by mass of AIBN as an initiator were added. Inert gas purge was performed three times in which the inside of the reactor was vacuumed and then nitrogen was introduced. After that, 160.0 parts by mass of MA purified by simple distillation and 480 parts by mass of toluene were added (corresponding to Initial Monomer in Table 1), followed by immersion of the reactor in a water bath and heating to have an internal temperature of 60° C. and stirring. Sampling was appropriately performed and the progress of the polymerization was checked from the solid concentration. When the conversion of MA reached 18 mass %, the polymerization was terminated by cooling to 30° C. At the conversion of 18%, the polymer had a number-average molecular weight (Mn) of 15,500. The reactor was connected to a vacuum line and the residual MA and toluene were distilled off under reduced pressure at 30° C.
[Synthesis of Block b]

After adding 640 parts by mass of VAc (corresponding to "Addition All at Once" of Additional Monomer in Table 1), the internal temperature was heated to 60° C. and stirred. Sampling was appropriately performed and the progress of the polymerization was checked from the solid concentration. When the conversion of VAc reached 22 mass %, 1.68 parts by mass of 1,1-DPEt was added as a polymerization inhibitor. In this situation, the number-average molecular weight (Mn) was 91,200.

The induction period until the polymerization of the block b was 5 hours, and the growth period until the addition of the inhibitor was 4 hours.

Subsequently, purification, saponification, and salt formation were performed by the same methods as in Example 1 to obtain an intended copolymer (A) (binary block copolymer of block c-block b). The evaluation results of the copolymer thus obtained are shown in Table 2.

TABLE 1

| | Initiator | | Control Agent | | | Initial Monomer | | | | Additional Monomer Addition All at Once | |
|---|---|---|---|---|---|---|---|---|---|---|---|
| | Type | Added Amount parts by mass | Type | Added Amount parts by mass | Polymerization Temperature °C. | Type | Added Amount parts by mass | Conversion [1] mass % | Mn [1] — | Type | Added Amount parts by mass |
| Example 1 | V70 | 0.67 | Co(acac)₂ | 0.19 | 30 | VAc | 500 | 19 | 129000 | MA | 7.8 |
| Example 2 | V70 | 0.27 | Co(acac)₂ | 0.07 | 30 | VAc | 500 | 10 | 172000 | MA | 17.1 |
| Example 3 | V70 | 0.67 | Co(acac)₂ | 0.19 | 30 | VAc | 500 | 13 | 86000 | MA | 1.3 |
| Example 4 | V70 | 0.67 | Co(acac)₂ | 0.19 | 30 | VAc | 500 | 13 | 86000 | AMPS | 3.1 |
| Example 5 | V70 | 0.67 | Co(acac)₂ | 0.19 | 30 | VAc | 500 | 13 | 86000 | MAPTAC | 3.3 |
| Example 6 [6] | V70 | 0.34 | Co(acac)₂ | 0.09 | 30 | VAc | 500 | 6 | 172000 | MA | 1.3 |
| Example 7 | V70 | 0.67 | Co(acac)₂ | 0.19 | 30 | VAc | 500 | 19 | 129000 | MA | 8 |
| Comparative Example 1 | AlBN | 0.15 | — | — | 60 | Vac, MA | 640 | 1.1 | — | — | — |
| Comparative Example 2 | V70 | 0.67 | Co(acac)₂ | 0.19 | 30 | VAc | 500 | 13 | 86000 | MA | 1.3 |
| Comparative Example 3 | V70 | 5.38 | Co(acac)₂ | 1.50 | 30 | VAc | 500 | 30 | 25800 | MA | 13.3 |
| Comparative Example 5 [7] | AlBN | 0.91 | Co(TMP) | 1.56 | 60 | MA | 160 | 18 | 15500 | VAc | 640 |

| | Additional Monomer Feed | | | Polymerization Inhibitor | | | | Induction Period (h) | Growth Period (h) | Type of Additive in Saponification Step |
|---|---|---|---|---|---|---|---|---|---|---|
| | Type | Added Amount parts by mass | Conversion [4] mass % | Type | Added Amount parts by mass | Conversion [5] mass % | Mn [5] — | | | |
| Example 1 | | — | | 1,1-DPEt | 0.66 | 26 | 182600 | 6 | 4 | NaOH |
| Example 2 | | — | | 1,1-DPEt | 0.26 | 21 | 368100 | 5 | 3 | NaOH |
| Example 3 | VAc, MA | 25, 6.2 | 18 | 1,1-DPEt | 0.66 | 22 | 161700 | 6 | 3 | NaOH |
| Example 4 | VAc, AMPS [2] | 25, 14.9 | 18 | 1,1-DPEt | 0.66 | 22 | 176200 | 6 | 4 | NaOH |
| Example 5 | VAc, MAPTAC [2] | 25, 15.8 | 18 | 1,1-DPEt | 0.66 | 22 | 177500 | 6 | 4 | NaOH |
| Example 6 [6] | VAc, MA | 13, 3.1 | 9 | 1,1-DPEt | 0.33 | 20 | 284900 | 6 | 3 | NaOH |
| Example 7 | | — | | 1,1-DPEt | 0.66 | 26 | 182600 | 6 | 4 | Ca(OH)₂ |
| Comparative Example 1 | MA [3] | 11.4 | 35 | p-benzoquinone | 0.15 | 35 | 172000 | 0 | 3 | NaOH |
| Comparative Example 2 | VAc, MA | 25, 6.2 | 18 | 1,1-DPEt | 0.66 | 22 | 161700 | 6 | 3 | AcOH |
| Comparative Example 3 | | — | | 1,1-DPEt | 5.24 | 38 | 33500 | 12 | 6 | NaOH |
| Comparative Example 5 [7] | | — | | 1,1-DPEt | 1.68 | 22 | 91200 | 5 | 4 | NaOH |

[1] Conversion and number-average molecular weight Mn of initial monomer immediately before adding additional monomer

[2] Added as methanol solution (Example 4: mass ratio (AMPS/MeOH) = 14.9/50, Example 5: mass ratio (MAPTAC/MeOH) = 18/50)

[3] 40 mass % aqueous solution of MA was added with time from polymerization initiation to polymerization termination.

[4] Total conversion of monomer at feed completion time

[5] Total conversion and number-average molecular weight Mn of monomer at the time point of adding polymerization terminator

[6] Block b-block c-block b triblock copolymer was obtained by continuing polymerization even after complete consumption of MA in comonomer. When MA was completely consumed, total conversion of monomer was 14 mass % and number-average molecular weight Mn was 198900.
[7] Polymerization was terminated at the MA conversion of 18%, and then MA and toluene were removed, and then VAc was added. Mn at the MA conversion of 18% was 15500. Polymerization was performed until the VAc conversion of 22%.

TABLE 2

| | $Mn_A$ | $Mn_b$ | $Mn_b/Mn_A$ | $DP_A$ | $DP_b$ | $Mw_A/Mn_A$ | Degree of Saponification mol % | Ionic Group | Counterion | $(Z_A)$ [1] | $(R_c)$ [2] |
|---|---|---|---|---|---|---|---|---|---|---|---|
| Example 1 | 99,800 | 66,100 | 0.66 | 2,200 | 1,500 | 1.30 | 99.9 | Carboxylic Acid | Na | 5.9 | 20.0 |
| Example 2 | 222,700 | 88,100 | 0.40 | 4,300 | 2,000 | 1.50 | 99.9 | Carboxylic Acid | Na | 16.0 | 30.0 |
| Example 3 | 88,800 | 44,100 | 0.50 | 1,900 | 1,000 | 1.30 | 99.9 | Carboxylic Acid | Na | 6.4 | 13.6 |
| Example 4 | 102,300 | 44,100 | 0.43 | 1,900 | 1,000 | 1.55 | 99.9 | Sulfonic Acid | Na | 6.4 | 13.6 |
| Example 5 | 103,800 | 44,100 | 0.42 | 1,900 | 1,000 | 1.55 | 99.9 | Ammonium | Cl | 6.3 | 13.6 |

TABLE 2-continued

| | | | | | | | | | | | |
|---|---|---|---|---|---|---|---|---|---|---|---|
| Example 6 | 153,000 | 88,100 | 0.58 | 3,400 | 2,000 | 1.40 | 99.9 | Carboxylic Acid | Na | 4.3 | 10.9 |
| Example 7 | 99,800 | 66,100 | 0.66 | 2,200 | 1,500 | 1.30 | 99.9 | Carboxylic Acid | Ca | 5.9 | 20.0 |
| Comparative Example 1 | 80,100 | 0 | — | 1,800 | 0 | 2.00 | 99.9 | Carboxylic Acid | Na | 5.1 | 5.1 |
| Comparative Example 2 | 88,800 | 44,100 | 0.50 | 1,900 | 1,000 | — | 99.9 | Carboxylic Acid | — | 6.4 | 13.6 |
| Comparative Example 3 | 18,500 | 13,300 | 0.72 | 400 | 300 | 1.30 | 99.9 | Carboxylic Acid | Na | 6.8 | 29.9 |
| Comparative Example 4 | | | | | — | | | | | | |
| Comparative Example 5 | 51,700 | 37,000 | 0.72 | 1,060 | 880 | 1.20 | 99.9 | Carboxylic Acid | Na | 17.0 | 100 |

| | $(J_A)^{3)}$ | $(K_c)^{4)}$ | $(Q_A)^{5)}$ | $(V_A)^{6)}$ | $(H_c)^{7)}$ | Absorbency DIW ratio (g/g) | saline ratio (g/g) | Saline Retentivity ratio (g/g) | Soluble Amount 20° C. mass % | 95° C. mass % | Bio-degradation Rate |
|---|---|---|---|---|---|---|---|---|---|---|---|
| Example 1 | 5.9 | 20.0 | 230.0 | 0.88 | 80.0 | 500 | 50 | 40 | >95 | >95 | — |
| Example 2 | 16.0 | 30.0 | 230.0 | 0.80 | 70.0 | 500 | 50 | 30 | >95 | >95 | — |
| Example 3 | 6.4 | 13.6 | 230.0 | 0.97 | 86.4 | 600 | 60 | 50 | >95 | >95 | — |
| Example 4 | 6.4 | 13.6 | 230.0 | 0.00 | 86.4 | 400 | 40 | 30 | >95 | >95 | — |
| Example 5 | 6.3 | 13.6 | 230.0 | 0.00 | 86.4 | 400 | 40 | 30 | >95 | >95 | — |
| Example 6 | 4.3 | 10.9 | 230.0 | 0.97 | 89.1 | 600 | 60 | 60 | >95 | >95 | 50 |
| Example 7 | 5.9 | 20.0 | 230.0 | 0.88 | 80.0 | 400 | 40 | 40 | >95 | >95 | — |
| Comparative Example 1 | 5.1 | 5.1 | 208.0 | 0.99 | — | 100 | 10 | 0 | >95 | >95 | 50 |
| Comparative Example 2 | 0.0 | 0.0 | 230.0 | 0.97 | 86.4 | 0 | 0 | 0 | 5 | 90 | — |
| Comparative Example 3 | 6.8 | 29.9 | 230.0 | 0.77 | 70.1 | 200 | 20 | 20 | >95 | >95 | — |
| Comparative Example 4 | | | — | | | 600 | 60 | 60 | 0 | 0 | <5 |
| Comparative Example 5 | 17.0 | 100 | 225.0 | 0.00 | 0.0 | 300 | 30 | 30 | >95 | >95 | — |

$^{1)}$Content of unit derived from ionic monomer in block copolymer (A)
$^{2)}$Content of unit derived from ionic monomer in polymer block (c)
$^{3)}$Content of salt forming ionic monomer unit in block copolymer (A)
$^{4)}$Content of salt forming ionic monomer unit in polymer block (c)
$^{5)}$Crystalline melting temperature
$^{6)}$Molar ratio ($V_A$) (lactone ring/total of acrylic acid monomer units and lactone ring) in acid-treated block copolymer
$^{7)}$Content of unit derived from vinyl alcohol-based monomer in polymer block (c)

The block copolymers (A) in Examples 1 through 7 were excellent in the absorbency of DIW and saline and the saline retentivity (gel shape retentivity) while also excellent in the water dissolution rate (water solubility). Although the bio-degradation rate was measured only in Example 6, it is considered that all Examples 1 through 8 exhibit equally good biodegradation rates.

The copolymer in Comparative Example 1 was a random copolymer not having the block (b) and the block (c). The copolymer in Comparative Example 2 was a copolymer having the block (b) but not having the ionic polymer block (c) containing a monomer unit with an ionic group forming a salt. The copolymer in Comparative Example 3 was a copolymer with $Mn_A$ of less than 20,000 and $Mn_b$ of less than 15,000. The copolymer in Comparative Example 5 was a copolymer with the ionic polymer block (c) containing no vinyl alcohol-based monomer units. The copolymers in Comparative Examples 1 through 3 and 5 were not sufficient in the absorbency of DIW and saline and the saline reten-tivity. In addition, the copolymer in Comparative Example 2 was also inferior in the water dissolution rate. The poly-acrylic acid-based superabsorbent resin in Comparative Example 4 did not have the block (b), and while excellent in the water absorption performance and the like, was inferior in the water dissolution rate (water solubility) and also poor in the biodegradation rate.

The invention claimed is:
1. A block copolymer (A), comprising:
a vinyl alcohol-based polymer block (b); and
an ionic polymer block (c) comprising (c-i) a first mono-mer unit comprising an ionic group forming a salt and (c-ii) a vinyl alcohol-based monomer unit,
wherein the ionic group is a carboxylic acid group, a sulfonic acid group, or an ammonium group,
wherein the vinyl alcohol-based polymer block (b) has a number-average molecular weight ($Mn_b$) in a range of from 15,000 to 220,000,
wherein the ionic polymer block (c) comprises the vinyl alcohol-based monomer unit (c-ii) in a range of from 5 to 95 mol. %, based on total monomer units,
wherein the block copolymer (A) has a number-average molecular weight ($Mn_A$) in a range of from 20,000 to 440,000, and
wherein an $Mn_b/Mn_A$ ratio of the number-average molecular weight ($Mn_b$) to the number-average molecular weight ($Mn_A$) is in a range of from 0.1 to 0.9.
2. The block copolymer (A) of claim 1, wherein the ionic group is the carboxylic acid group.
3. The block copolymer (A) of claim 1, wherein a counterion of the ionic group is an ion of an element in Group 1, 2, 12, 13, or 17 of the periodic table.

4. The block copolymer (A) of claim 1, wherein the block copolymer (A) has a content ($J_A$) of the first monomer unit (c-i) in a range of from 2 to 90 mol. %, based on the total monomer units.

5. The block copolymer (A) of claim 1, wherein the ionic polymer block (c) has a content ($K_c$) of the first monomer unit (c-i) in a range of from 5 to 95 mol. %, based on the total monomer units.

6. The block copolymer (A) of claim 1, wherein the block copolymer (A) has a degree of saponification in a range of from 80 to 99.99 mol. %.

7. The block copolymer (A) of claim 1, wherein the block copolymer (A) has a molecular weight distribution ($Mw_A/Mn_A$) in a range of from 1.05 to 1.95.

8. The block copolymer (A) of claim 1, wherein the block copolymer (A) is biodegradable.

9. The block copolymer (A) of claim 1, which absorbs 20 g or more of deionized water per 0.1 g of the block copolymer (A) at 20° C.

10. The block copolymer (A) of claim 1, which absorbs 20 g or more of a 0.9 mass % aqueous sodium chloride solution per 1 g of the block copolymer (A) at 20° C.

11. The block copolymer (A) of claim 1, wherein, when the block copolymer (A) is dissolved in water at 95° C., a soluble amount is 95 mass % or more.

12. The block copolymer (A) of claim 11, wherein, when the block copolymer (A) is dissolved in water at 20° C., a soluble amount is 95 mass % or more.

13. An absorber, comprising:
the block copolymer (A) of claim 1.

14. The absorber of claim 13, in the form of particles.

15. An absorbent article, comprising:
the absorber of claim 13.

16. The absorbent article of claim 15, which is a sanitary, commodity, construction, civil engineering, industrial, agricultural, medical, or food application article.

17. A method for producing the block copolymer (A) of claim 1, comprising:
polymerizing a vinyl ester monomer and copolymerization of a vinyl ester monomer and an ionic monomer with an ionic group or a derivative thereof by controlled radical polymerization in the presence of a radical polymerization initiator and a control agent to obtain a vinyl ester-based block copolymer comprising a vinyl ester polymer block (b1) and an ionic polymer block (c1) comprising a vinyl ester monomer unit and an ionic monomer unit; and
saponifying vinyl ester monomer units in the vinyl ester-based block copolymer obtained in the polymerizing to form vinyl alcohol monomer units.

18. The method of claim 17, wherein the control agent is an organic cobalt complex.

19. The method of claim 17, further comprising:
forming a salt of the ionic monomer unit.

20. The block copolymer (A) of claim 1, wherein the ionic group is the carboxylic acid group, and
wherein the block copolymer (A) has a content ($J_A$) of the first monomer unit (c-i) in a range of from 2 to 90 mol. %, based on the total monomer units.

* * * * *